Oct. 16, 1962 R. L. BYRUM Plant Pat. 2,183
ROSE PLANT
Filed Nov. 17, 1961
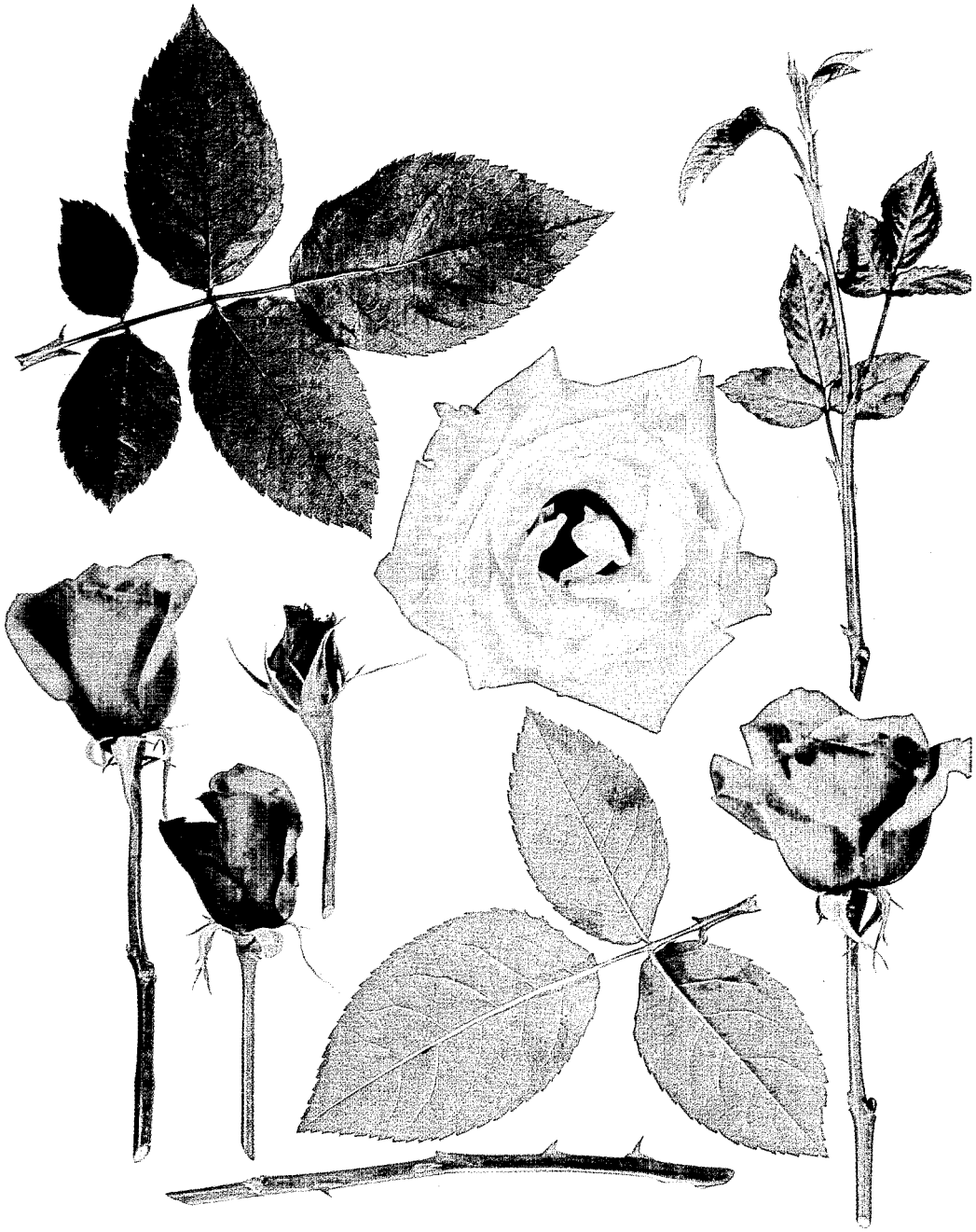
INVENTOR
Roy L. Byrum
BY Robb & Robb
ATTORNEYS United States Patent Office Plant Pat. 2,183
Patented Oct. 16, 1962

2,183
ROSE PLANT

Roy L. Byrum, Richmond, Ind., assignor to Joseph H. Hill Company, Richmond, Ind., a corporation of Indiana Filed Nov. 17, 1961, Ser. No. 153,247
1 Claim. (Cl. 47—61)

The present invention relates to a new and distinct variety of rose plant of the hybrid tea class, which was originated by me by crossing the variety "Topper" (Plant Patent No. 1,566) with an unnamed and unpatented seedling of unidentified parentage, but which is identified in my breeding records as #53–9R.

The primary objective of this breeding was to produce a new rose variety which retains the flower productivity of the seed parent, "Topper," but which bears flowers of improved size and color, while at the same time combining with these characteristics a more continuous flower production, with longer life of the flowers as cut flowers. In addition to the foregoing objectives, it was also my purpose to achieve greater resistance of the new variety to mildew and other rose plant diseases. These objectives were substantially achieved along with other desirable improvements, as evidenced by the following characteristics which are outstanding in the new variety and which distinguish it from its parents, as well as from all other varieties of which I am aware:

(1) Good growing and flower producing habits;

(2) An abundance of glossy green foliage extending well up on the neck of the flower stems;

(3) Relatively large flowers which are borne on strong stems of medium length;

(4) Good flower form, especially when open;

(5) Good flower fragrance;

(6) Better than average disease resistance, particularly with respect to mildew, as compared with other varieties grown under comparable cultural conditions at Richmond, Indiana;

(7) A distinctive, attractive and brilliant general color tonality of the flowers corresponding to Turkey Red in the newly open flowers, and to near Delft Rose in the three-days open flowers; and (8) Good keeping qualities of the flowers as cut flowers.

In comparison with its seed parent, "Topper," the new variety has more glossy foliage; it is more disease resistant, particularly with respect to mildew; bears larger flowers, with the flowers having short peduncles; the flowers are all of better form in both the bud and open stages and are more fragrant; the flower color is better and more brilliant; and the flowers have better keeping qualities as cut flowers.

As compared with the unnamed seedling pollen parent, the new variety is a better grower and better flower producer.

Asexual reproduction of my new variety by grafting, as performed at Richmond, Indiana, and also by budding as performed at West Grove, Pennsylvania, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson"), and Koster's Color Guide (hereinafter abbreviated as "Koster"), except where general color terms of ordinary dictionary significance are obvious:

Type: Bush; seedling.
Class: Hybrid tea.
Breeding: Seedling.
*Seed parent.*—"Topper."
*Pollen parent.*—An unnamed seedling of unidentified parentage.
Propagation: Holds its distinguishing characteristics through succeeding propagations by both grafting and budding.

*Flower*

Locality where grown and observed: Richmond, Indiana.
Flowers borne: Singly to stem; on strong stems of medium length.
Quantity of bloom: Abundant, in greenhouse.
Continuity: Continuous, in greenhouse.
Fragrance: Good. Nature—tea.
Bud:
*Peduncle.*—Short; medium diameter; strong; erect. Bark—entirely smooth. Color—Scheeles Green, Plate 860/1 (Wilson). Thorns—none. Prickles—none. Hairs—none.
*Before calyx breaks.*—Size—medium small. Form—short-pointed; without conspicuous neck; with foliaceous apendages on the surface of the bud; with slender foliaceous parts extending beyond the tip of the bud equal to ¾ or more of its length. Color—from Scheeles Green, Plate 860 (Wilson) through Scheeles Green, Plate 860/1 (Wilson).
*As calyx breaks.*—Color (outside of petal)—Indian Lake, Plate 826 (Wilson).
*As first petal opens.*—Sibe—medium large. Form—ovoid. Color: outside—base of petal Oxblood Red, Plate 00823 (Wilson), changing through Oxblood Red, Plate 00823/1 (Wilson), and gradually changing to Currant Red, Plate 821/1 (Wilson); inside—Blood Red, Plate 820/2 (Wilson), with veins of Blood Red, Plate 820 (Wilson), and also with white streak extending from base of petal approximately half way up petal.
*Opening.*—Opens up well in greenhouse; no unusual charactertstics attributed to weather conditions.
Bloom:
*Size (when fully open).*—Medium large; from 4 inches to 4½ inches.
*Petalage.*—Double (more petals, but the stamens not hidden); from 25 to 35 petals; arranged regularly.
*Form.*—Full and high-centered at first, but becoming open; petals being at first tightly rolled outward, but later becoming loosely rolled outward at maturity.
Petals:
*Texture.*—Thick; leathery. Inside—satiny. Outside—shiny.
*Shape.*—Outer petals—obovate, with apex obtuse. Intermediate petals—obovate, with apex obtuse. Inner petals—obovate, with apex round, and some with one notch.

This description of a newly opened flower was made from a rose grown in a greenhouse during the month of May at Richmond, Indiana:

*Color.*—Outer petal: outside surface—base of petal Currant Red, Plate 821 (Wilson), gradually changing through Currant Red, Plate 821/1 (Wilson) and through Currant Red, Plate 821/2 (Wilson) to Currant Red, Plate 821/3 (Wilson) at top of petal; inside surface—base of petal Cardinal Red, Plate 822/3 (Wilson), with remainder Orient Red, Plate 819/2 (Wilson), and also with veins of Blood Red, Plate 820/2 (Wilson). Intermediate petal: outside surface—base of petal Cardinal Red, Plate 822/3 (Wilson), changing through Currant Red, Plate 821/2 (Wilson) to Currant Red, Plate 821/3 (Wilson); inside surface—base of petal Cardinal Red, Plate 822/3 (Wilson), with remainder Geranium Lake, Plate 20/1 (Wilson). Inner petal: outside surface—base of petal Cardinal Red, Plate 822/3 (Wilson), gradually changing through Turkey Red, Plate 721/2 (Wilson) to Turkey Red, Plate 721/3 (Wilson); inside surface—base of petal Cardinal Red, Plate 822/3 (Wilson), with remainder Delft Rose, Plate 020/1 (Wilson).

This description was made from a rose that was open for three days in a greenhouse during the month of July at Richmond, Indiana:

*Color.*—Outer petal: outside surface—near Currant Red, Plate 821/3 (Wilson); inside surface—slightly lighter than Turkey Red, Plate 721/3 (Wilson). Intermediate petal: outside surface—near Turkey Red, Plate 721/3 (Wilson); inside surface—near Delft Rose, Plate 020/1 (Wilson). Inner petal: outside surface—near Turkey Red, Plate 721/3 (Wilson); inside surface—near Delft Rose, Plate 020/1 (*Wilson*).

*General color effect.*—Newly opened flower—Turkey Red, Plate 721/2 (Wilson). Three days open—near Delft Rose, Plate 020/1 (Wilson).

*Behavior of petals.*—Persist in greenhouse; no unusual characteristics attributed to weather conditions; fading from China Rose, Plate 024/1 (Wilson) to China Rose, Plate 024/2 (Wilson).

*Flower longevity.*—Cut roses grown in greenhouse and kept at living room temperatures—from 4 to 6 days in October and November.

*Reproductive Organs*

Stamens: Many; arranged regularly about pistils.

Filaments: Some short and some medium length; most with anthers. Color—Oxblood Red, Plate 00823 (Wilson).

Anthers: Medium large; all open at once. Color—Spanish Orange, Plate 010/2 (Wilson).

Pollen: Abundant. Color—Cadmium Orange, Plate 8/1 (Wilson).

Pistils: Many.

Styles: Uneven; medium length; moderately thin; bunched. Color—Spinel Red, Plate 0023/1 (Wilson).

Stigma: Color—Pure White, Plate 1 (Koster).

Ovularies: Most protruding from calyx.

Hips: None observed.

Sepals: Permanent; medium length; some straight and some spear-shaped. Color: inside—Scheeles Green, Plate 860/3 (Wilson), overlaid with white fuzz; outside—Spinach Green, Plate 0960/2 (Wilson).

Seeds: None.

*Plant*

Foliage:

*Leaves.*—Compound of 5–7 leaflets; abundant; medium large size; moderately heavy.

*Leaflets.* — Shape — ovoid. Apex — acute. Base —round. Margin—serrate.

*Color.*—Mature: upper surface — near Parsley Green, Plate 00962 (Wilson); under surface—near Cedar Green, Plate 80 (Koster). Young: upper surface—near Moss Green, Plate 96 (Koster), very slightly overlaid with Violet, Plate 59 (Koster) toward edge; under surface—near Moss Green, Plate 96 (Koster), overlaid with Violet Plate 59 (Koster).

*Rachis (the supporting stem of the compound leaf).*—Medium heavy. Upper side—almost smooth; grooved. Under side—smooth surface; with thorns.

*Stipules.*—Medium length; narrow; with short points turning out at an angle less than 45°.

Growth:

*Habit.*—Bush; upright; much-branched.

*Growth.*—Free; vigorous.

*Canes.*—Medium diameter.

*Main stems.*—Color—Spinach Green, Plate 0960 (Wilson), overlaid with streaks of Van Dyck Brown, Plate 96 (Koster). Thorns—several; medium length; hooked downward; with long, narrow base; color—Bistre, Plate 93 (Koster). Prickles—none. Hairs—none.

*Branches.*—Color—Spinach Green, Plate 0960/1 (Wilson). Thorns — several; medium length; hooked downward; with long, narrow base; color —near Reseda, Plate 85 (Koster). Prickles—several; color—near Reseda, Plate 85 (Koster), Hairs—none.

*New shoots.*—Color—Scheeles Green, Plate 860/2 (Wilson). Thorns — several; medium length; hooked downward; with long, narow base; color —Fern Green, Plate 0862/3 (Wilson). Prickles—few; color—Fern Green, Plate 0862/3 (Wilson). Hairs—none.

I claim:

A new and distinct variety of rose plant of the hybrid tea class, substantially as herein shown and described, characterized particularly as to novelty by the unique combination of good growing and flower producing habits, abundant glossy green foliage extending well up on the neck of the flower stems, relatively large flowers which are borne on strong stems of medium length, good flower form, especially when open, good flower fragrance, better than average disease resistance, particularly with respect to mildew, a distinctive, attractive and brilliant general color tonality of the flowers corresponding to Turkey Red in the newly open flowers, and to near Delft Rose in the three-days open flowers, and good keeping qualities of the flowers as cut flowers.

No references cited.